United States Patent [19]

Fields

[11] Patent Number: 5,098,395
[45] Date of Patent: Mar. 24, 1992

[54] MEDICAL CONNECTOR
[75] Inventor: Charlie B. Fields, Ypsilanti, Mich.
[73] Assignee: Tri-State Hospital Supply Corporation, Howell, Mich.
[21] Appl. No.: 624,046
[22] Filed: Dec. 7, 1990

Related U.S. Application Data

[63] Continuation-in-part of Ser. No. 592,134, Oct. 3, 1990.
[51] Int. Cl.$^5$ ............................................. A61M 5/178
[52] U.S. Cl. ..................................... 604/168; 604/900
[58] Field of Search ............... 604/168, 167, 166, 165, 604/164, 283, 284, 256, 900, 905, 170, 171

[56] References Cited

U.S. PATENT DOCUMENTS

| | | | |
|---|---|---|---|
| 3,851,647 | 12/1974 | Monestere, Jr. et al. | 604/905 X |
| 4,398,544 | 8/1983 | Nugent et al. | 604/240 X |
| 4,417,886 | 11/1983 | Frankhouser et al. | 604/170 X |
| 4,511,359 | 4/1985 | Vaillancourt | 604/905 X |
| 4,547,194 | 10/1985 | Moorehead | 604/905 X |
| 4,752,292 | 6/1988 | Lopez et al. | 604/905 X |

Primary Examiner—John D. Yasko
Attorney, Agent, or Firm—Brooks & Kushman

[57] ABSTRACT

A medical connector (10) disclosed comprises a fist connector member (10) having an elongated hollow introducer needle (14). The introducer needle (14) has first and second end portions (16,18) and first and second spaced openings (20,22) to the hollow of needle (14) between the end portions (16,18). A second connector member (28) is connectable with the first connector member (12). The second connector member (28) includes a flashback chamber (30) having a rubber septum (32) and also a catheter tip (34) mounted thereon. The introducer needle (14) is axially movable through the rubber septum (32), flashback chamber (30), and catheter tip (34) to establish an opening in a patient's vein for placement of the catheter (34). The movement of the introducer needle (14) positions the first and second openings (20,22) within the flashback chamber (3) when the opening in the patient's vein is established whereby to provide venting of the needle (14) and flashback chamber (30) as the patient's blood is communicated through the first end portion (16) and into the flashback chamber (30) providing visual confirmation of a successful stick by the presence of blood within the flashback chamber (30) before all the air is displaced from the flashback chamber (30) to prevent the possibility of blood spillage to the second portion (18).

10 Claims, 1 Drawing Sheet

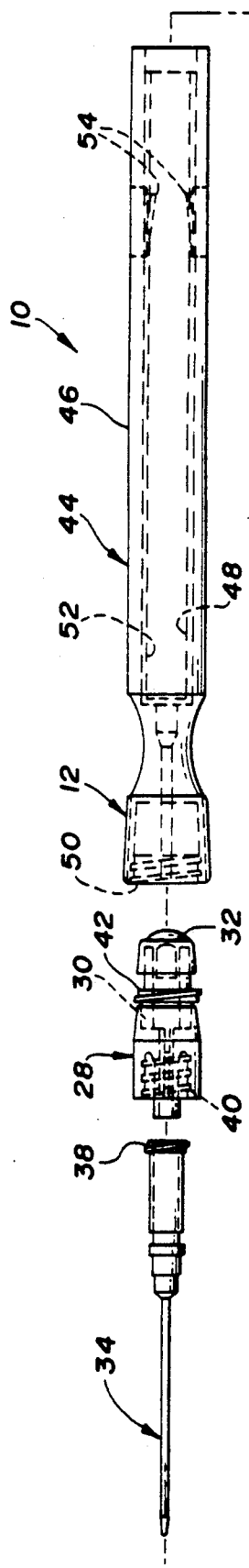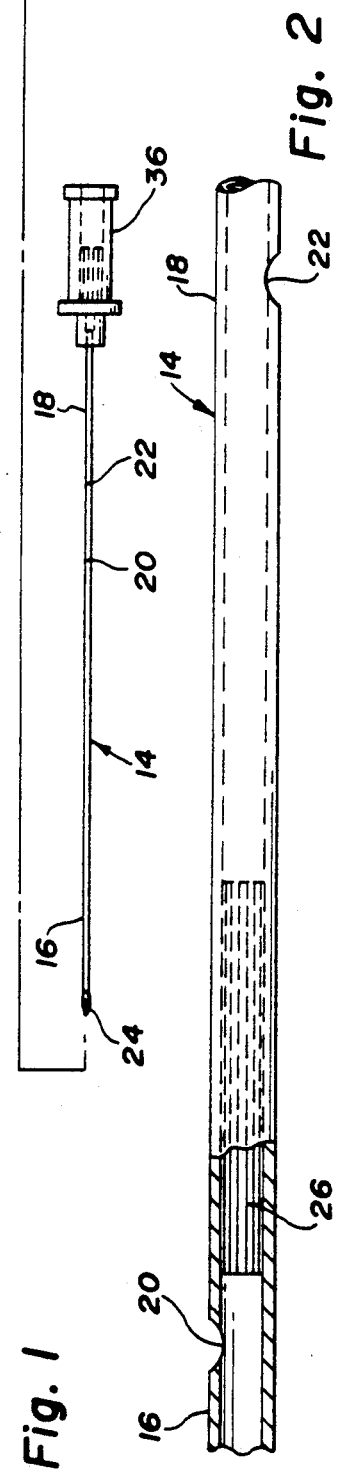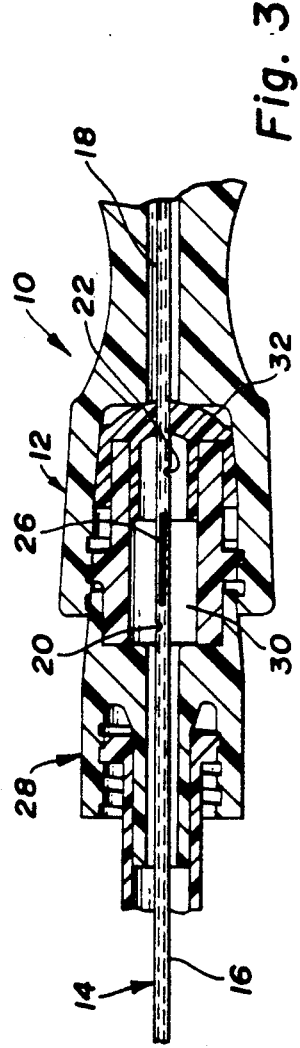

MEDICAL CONNECTOR

CROSS-REFERENCE TO RELATED APPLICATION

This invention is a continuation-in-part of prior application Ser. No. 592,134 which was filed on Oct. 3, 1990 in the name of Charlie B. Fields.

TECHNICAL FIELD

This invention relates to medical connectors for fluid carrying tubes, and more particularly, to medical connectors for connecting intravenous tubes to a patient's vein that minimize the risk of contact with the patient's blood.

BACKGROUND ART

Conventional medical connectors used to connect tubing used in intravenous delivery apparatus include a connector having at least two connector members. One of the connector members typically includes a needle and another of the connector members includes a sealed entry port that is penetratable by the needle to establish fluid communication between the members when the members are connected. The entry port usually comprises resilient material that automatically closes after the withdrawal of the needle.

Typically, the needle is recessed in the cavity of one member so that after termination of the connection, the needle that has been in contact with the patient's blood is not easily contacted by a nurse who is at risk from being stuck by a contaminated needle. Such connectors are disclosed in U.S. Pat. Nos. 4,752,292 and 4,511,359.

These conventional medical connectors however, make no provision preventing a recessed needle from contact with the patient's blood, where the needle could become contaminated.

U.S. Pat. No. 4,511,359 discloses a one-way valve comprised of a biased tubular band fit over a perforated projection permitting pressurized fluid flow in only one direction to keep a fluid connector sterile. The perforated projection therein is impermeable to the introduction of an introducer needle rendering the connector unsuitable for use with a catheter tip. However, the valve structure can be improved upon.

Also, when one of the connector members is fitted with a catheter for placement in the patient's vein and the other connector member is fitted with a movably mounted introducer needle for establishing an opening in the patient's vein to place the catheter, blood flow through the needle and out its other end after a stick indicates whether the venous placement is correct. This blood flow is stopped by disposing of the connector member with the introducer needle and connecting another connector member that is in communication with an intravenous line; however, this exposure to the patient's blood is undesirable.

Conventional needles have a hydrophobic filter membrane to allow air to flow through the hollow of the needle but not blood. Use of such a needle requires that it be removed from the catheter to verify whether a proper insertion in the vein has been effected. With the removal of the needle, blood flows out from the catheter and is contactable by a user.

SUMMARY OF THE INVENTION

An object of the present invention is to provide a catheter over needle connector assembly which prevents exposure of a patient's blood to a user of the assembly.

A further object of the invention is to provide a vented introducer needle and flashback chamber assembly in combination with a catheter that eliminates the necessity of removing the introducer needle from the catheter to determine whether proper venous placement has been established.

In carrying out the above objects and other objects of the invention, the medical connector for connecting a fluid carrying tube to the patient's vein comprises a first connector member having an elongated hollow introducer needle movably mounted by the first connector member. The introducer needle has first and second end portions and first and second spaced openings to the hollow of the needle between the end portions. The first end portion includes a tip for venipuncture. The introducer needle further includes a plug portion between the first and second spaced openings for plugging communication between the first and second end portions.

A second connector member, connectable with the first connector member, includes a flashback chamber having a rubber septum. The flashback chamber also includes a catheter tip mounted thereon. The introducer needle is axially movable through the rubber septum, flashback chamber and catheter tip to establish an opening in the patient's vein for placement of the catheter.

The movement of the introducer needle positions the first and second openings within the flashback chamber when the opening in the patient's vein is established whereby venting of the needle and flashback chamber is provided as the patient's blood is communicated through the first end portion and into the flashback chamber through the first opening to displace air from the flashback chamber through the second opening. This provides for a visual confirmation of a successful stick by the presence of blood within the flashback chamber before the air is displaced from the flashback chamber preventing the possibility of blood spillage to the second portion of the needle.

In the preferred embodiment of the invention, the spaced openings in the introducer needle are generally 1.5 centimeters apart. The introducer needle includes a hub mounted on the second end portion that includes a hydrophobic filter membrane that allows air to flow through the membrane but not blood. The catheter has a female luer hub on its proximal end to allow connection to a standard intravenous line and the flashback chamber has a male luer lock feature on its distal end to affix the flashback chamber to the catheter.

The flashback chamber includes connecting means for connecting various connector members to form a connector system. The first connector member includes a needle guard including a shield means having a track that generally envelops the needle while allowing the user to grasp the needle hub for movement along the track. The guard has a connector means that allows the guard to be connected to the flashback chamber. The guard includes a guide which guides the needle for accurate axial movement. The guide further includes stop means for securing the hub of the needle as the needle is retracted to a retracted position with the tip of the needle housed within the guard.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is an exploded plan view of a medical connector having first and second connector members and including a vented hollow introducer needle and flashback chamber constructed in accordance with the present invention;

FIG. 2 is a partial sectional view of the vented needle of FIG. 1 illustrating first and second spaced openings and a plug portion therebetween; and FIG. 3 is an enlarged partial sectional view of the connector illustrating the positioning of the first and second openings in the flashback chamber when an opening in a patient's vein is established.

BEST MODE FOR CARRYING OUT THE INVENTION

With reference to FIG. 1 of the drawings, a medical connector is generally indicated by reference numeral 10 and is used for connecting a fluid carrying tube to a patient's vein.

In my earlier U.S. patent application Ser. No. 592,134, which is hereby incorporated by reference, I disclosed numerous embodiments of medical connectors which form a system for quickly and safely connecting a fluid carrying tube to a patient. As is hereinafter more fully described, the connector 10 is a further improvement upon the catheter over needle embodiment of my earlier application. The connector 10 provides visual evidence of successful venous placement without removing the introducer needle and also provides a needle for use in other systems that reduces the risk of contact with a patient's blood.

With reference to FIGS. 1-3, the medical connector 10 comprises a first connector member 12 having an elongated hollow introducer needle 14 movably mounted by the first connector member. The introducer needle 14 has first and second end portions 16,18 and first and second spaced openings 20,22 to the hollow of the needle between the end portions. The first end portion 16 includes a tip 24 for venipuncture.

With reference to FIG. 2, the introducer needle 14 further also includes a plug portion 26 between the first and second spaced openings 20,22 for plugging communication between the first and second end portions 16,18.

In FIGS. 1 and 3, a second connector member 28 is connectable with the first connector member 12. The second member 28 includes a flashback chamber 30 having a rubber septum 32. The flashback chamber 30 also includes a catheter tip 34 mounted thereon. The introducer needle 14 is axially movable through the rubber septum 32, flashback chamber 30, and catheter tip 34 to establish an opening in the patient's vein for placement of the catheter.

With reference to FIG. 3, the movement of the introducer needle 14 positions the first and second openings 20,22 within the flashback chamber 30 when the opening in the patient's vein is established. This positioning provides venting of the needle 14 and flashback chamber 30 as the patient's blood is communicated through the first end portion 16 and into the flashback chamber 30 through the first opening 20. In this way, air is displaced from the flashback chamber 30 through the second opening 22 and visual confirmation of a successful stick is provided by the presence of blood within the flashback chamber 30 before all the air is displaced from the flashback chamber 30 to prevent the possibility of blood spillage to the second portion 18.

With continued reference to FIG. 1 of the drawings, the introducer needle 14 includes a hub 36 mounted on the second end portion 18. Hub 36 includes a hydrophobic filter membrane that allows air to flow out from the needle but not blood.

Referring again to FIGS. 1 and 3, the catheter 34 has a female luer hub 38 on its proximal end to provide connection to a standard intravenous line if necessary. The flashback chamber 30 has a male luer lock feature 40 on its distal end to affix the flashback chamber to the catheter 34. The flashback chamber 30 includes connecting means 42, shown as a screw thread attachment, for connecting various connector members such as the connectors disclosed in my earlier application.

Preferably, the first connector member 12 includes a needle guard 44 including a shield means 46 having a track 48 that generally envelops the needle 14 while allowing the user to grasp the needle hub for movement along the track. Guard 44 has connector means 50 that allow the guard to be connected to the flashback chamber 30. Guard 44 includes a guide 52 which guides the needle 14 for accurate axial movement as the needle is moved by the user. Guard 44 includes stop means 54 for securing the hub 36 of needle 14 as the needle is retracted to a retracted position with the tip 24 concealed within the guard.

While the best mode for carrying out the invention has been described in detail, those familiar with the art to which this invention relates will recognize various alternative designs and embodiments for practicing the invention as defined by the following claims.

What is claimed is:

1. A medical connector for connecting a fluid carrying tube to a patient's vein, the medical connector comprising:

a first connector member having an elongated hollow introducer needle movably mounted by said first connector member; said introducer needle having first and second end portions and first and second spaced openings to the hollow of the needle between said end portions; said first end portion including a tip for venipuncture; said introducer needle further including a plug portion between said first and second spaced openings for plugging communication between said first and second end portions; and a second connector member connectable with said first connector member; said second connector member including a flashback chamber having a rubber septum and also including a catheter tip mounted thereon; said introducer needle being axially movable through said rubber septum, flashback chamber and catheter tip to establish an opening in the patient's vein for placement of said catheter; the movement of said introducer needle positioning said first and second openings within said flashback chamber when the opening in the patient's vein is established whereby to provide venting of said needle and flashback chamber as the patient's blood is communicated through said first end portion and into said flashback chamber through said first opening to displace air from said flashback chamber through said second opening thereby providing visual confirmation of a successful stick by the presence of blood within said flashback chamber before the air is displaced therefrom to prevent the possibility of blood spillage to said second portion.

2. A medical connector as in claim 1 wherein said spaced openings in said introducer needle are generally 1.5 cm apart.

3. A medical connector as in claim 1 wherein said introducer needle includes a hub mounted on said second end portion; said hub including a hydrophobic filter membrane that allows air to flow through but not blood.

4. A medical connector as in claim 1 wherein said catheter has a female luer hub on its proximal end to allow connection to a standard intravenous line.

5. A medical connector as in claim 4 wherein said flashback chamber has a male luer lock feature on its distal end to affix said flashback chamber to said catheter.

6. A medical connector as in claim 5 wherein said flashback chamber includes connecting means for connecting various connector members.

7. A medical connector as in claim 1 wherein said first connector member includes a needle guard including a shield means having a track that generally envelops said needle while allowing a user to grasp said needle hub for movement along said track.

8. A medical connector as in claim 7 wherein said guard has connector means that allow said guard to be connected to said flashback chamber.

9. A medical connector as in claim 8 wherein said guard includes a guide which guides said needle for accurate axial movement.

10. A medical connector as in claim 9 wherein said guard includes stop means for securing said hub of said needle as said needle is retracted to a retracted position with said tip concealed within said guard.

* * * * *